United States Patent [19]

Junino et al.

[11] Patent Number: 5,534,036

[45] Date of Patent: Jul. 9, 1996

[54] KERATINOUS FIBER DYEING METHODS AND COMPOSITIONS WHICH CONTAIN SULFATED METHAPHENYLENEDIAMINE COUPLERS IN COMBINATION WITH OXIDATION DYE PRECURSORS

[75] Inventors: Alex Junino, Livry-Gargan; Alain Lagrange, Chatou; Alain Genet, Aulnay-sous-Bois, all of France

[73] Assignee: L'Oreal, Paris, France

[21] Appl. No.: 357,745

[22] Filed: Dec. 16, 1994

Related U.S. Application Data

[63] Continuation of Ser. No. 130,902, Oct. 4, 1993, abandoned.

[30] Foreign Application Priority Data

Oct. 2, 1992 [FR] France ................................. 92 11711

[51] Int. Cl.⁶ ..................................................... A61K 7/13
[52] U.S. Cl. ........................... 8/411; 8/406; 8/407; 8/408; 8/410; 8/412; 8/416
[58] Field of Search ................................. 8/405, 406, 408, 8/410, 411, 416, 407, 412

[56] References Cited

U.S. PATENT DOCUMENTS

| | | | |
|---|---|---|---|
| 1,940,757 | 12/1933 | Lehmann et al. | 8/408 |
| 4,595,742 | 6/1986 | Nalepa et al. | 528/64 |
| 4,631,298 | 12/1986 | Presswood | 521/163 |
| 4,973,760 | 11/1990 | Davis | 564/440 |
| 4,982,002 | 1/1991 | McKinnie et al. | 564/440 |

FOREIGN PATENT DOCUMENTS

| | | |
|---|---|---|
| 253593 | 1/1988 | European Pat. Off. . |
| 1061331 | 4/1954 | France . |
| 2687308 | 8/1993 | France . |
| 1165811 | 3/1964 | Germany . |
| 3343642 | 6/1985 | Germany . |
| 9222525 | 12/1992 | WIPO . |

OTHER PUBLICATIONS

Translation of West German Patent No. 3,343,642, Henkle KGaA, Jun. 1985.

Gosnell et al, "An ortho-thioalkylated aromatic diamine as an improved liquid hardener for carbon fiber reinforced epoxy matrices", Int. Sampe Symp. Exhib. vol. 33, Mar. 1988, pp. 746–753.

Croft, "Fluoroalkylthio substituted aromatic derivatives", Phosphorus and Sulfur, 1976, vol. 2, pp. 133–139. No month available.

*Primary Examiner*—Paul Lieberman
*Assistant Examiner*—Caroline L. Dusheck
*Attorney, Agent, or Firm*—Cushman Darby & Cushman

[57] ABSTRACT

The present invention provides compositions of sulfated metaphenylenediamines for dyeing keratinous fibers and methods for their use.

11 Claims, No Drawings

KERATINOUS FIBER DYEING METHODS AND COMPOSITIONS WHICH CONTAIN SULFATED METHAPHENYLENEDIAMINE COUPLERS IN COMBINATION WITH OXIDATION DYE PRECURSORS

This is a continuation of application Ser No. 08/130,902, filed Oct. 4, 1993, now abandoned.

BACKGROUND OF THE INVENTION

1. Field of the Invention

The present invention relates to the use of sulfated metaphenylenediamines in dyeing keratinous fibers, in particular human hair, to dye compositions containing these sulfated metaphenylenediamines, to a dyeing method using these compositions and to novel sulfated metaphenylenediamines and their preparation process.

2. Description of the Prior Art

Sulfated aromatic amine derivatives associated with oxidation dye precursors are already used to dye keratinous fibers.

It is known to dye keratinous fibers, in particular human hair, using dye compositions containing oxidation dye precursors and coupling agents.

Coupling agents, also known as color modifiers, allow the tints obtained with the oxidation dye precursors to be varied.

In the field of dyeing keratinous fibers, in particular human hair, coupling agents are always being sought which, when associated with oxidation dye precursors, produce a wide range of hair tints which have satisfactory resistance to light, washing, bad weather, perspiration and other hair treatments.

The applicants have discovered that dye compositions for keratinous fibers containing certain sulfated metaphenylenediamines as coupling agents with ortho and/or para type oxidation dye precursors and an oxidizing agent produce, after application to the keratinous fibers, in particular human hair, a wide range of tints which are remarkably resistant to light, washing, bad weather, perspiration and other hair treatments.

An object of the present invention is therefore the use of sulfated metaphenylenediamines as defined below to dye keratinous fibers, in particular human hair.

The invention also provides oxidation dye compositions for use in dyeing keratinous fibers, in particular human hair, containing at least one ortho and/or para type oxidation dye precursor and at least one sulfated metaphenylenediamine having formula (I) as defined below.

The invention further provides a method of dyeing keratinous fibers, in particular human hair, using such a composition mixed with an oxidizing agent.

The invention also relates to novel sulfated metaphenylenediamines and to their preparation process.

Further objects of the invention will become apparent from the description and examples given hereinafter.

SUMMARY OF THE INVENTION

In one aspect the present invention consists in the use of at least one sulfated metaphenylenediamine having the general formula:

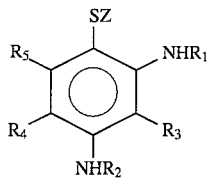

for dyeing keratinous fibers, in particular human hair, wherein: Z represents a $C_1$–$C_{18}$ alkyl radical, an aralkyl radical wherein the alkyl radical is $C_1$–$C_6$, a $C_1$–$C_6$ monohydroxyalkyl or $C_2$–$C_6$ polyhydroxyalkyl radical, an aryl radical, a $C_1$–$C_4$ fluoroalkyl radical, an aminoalkyl radical having the formula:

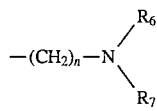

wherein n is a whole number from 1 to 6 inclusive; $R_6$ and $R_7$, which may be identical or different, represent a hydrogen atom or a $C_1$–$C_4$ alkyl radical, a $C_1$–$C_4$ hydroxyalkyl radical or a $C_1$–$C_6$ acyl radical;

$R_1$ and $R_2$, which may be identical or different, represent a hydrogen atom, a $C_1$–$C_6$ alkyl radical, a $C_1$–$C_6$ monohydroxyalkyl radical, a $C_2$–$C_6$ polyhydroxyalkyl radical, a $C_1$–$C_6$ monocarbamylalkyl radical, a $C_1$–$C_6$ dialkylcarbamyl radical, a $C_1$–$C_6$ aminoalkyl radical, an acylaminoalkyl ($C_1$–$C_4$) radical, a carbalkoxy($C_2$–$C_6$)alkyl($C_1$–$C_4$) radical, a $C_1$–$C_6$ carbamyl or monoalkyl radical or a $C_1$–$C_4$ fluoroalkyl radical;

$R_3$ represents a hydrogen atom or a $C_1$–$C_4$ alkyl radical;

$R_4$ and $R_5$, which may be identical or different, represent a hydrogen atom, a $C_1$–$C_4$ alkyl radical, a $C_1$–$C_4$ alkoxy radical, a $C_1$–$C_4$ hydroxyalkyl radical, a halogen or a —SZ radical where Z has the meaning described above, and at least one of the radicals $R_3$, $R_4$ or $R_5$ is other than a hydrogen atom, and their acid salts.

Among the preferred designations for radical Z in sulfated metaphenylenediamines having general formula (I), the $C_1$–$C_{18}$ alkyl radical may designate methyl, ethyl, propyl, butyl, dodecyl or hexadecyl; the aralkyl radical may designate benzyl; the mono or polyhydroxyalkyl radical may designate —$CH_2$—$CH_2OH$, —$CH_2$—$CHOH$—$CH_2OH$, —$CH_2$—$CHOH$—$CH_3$; the aryl radical may designate phenyl, the aminoalkyl radical may designate —$CH_2$—$CH_2$—$NH_2$, —$CH_2$—$CH_2$—$NHCH_3$; the acylaminoalkyl radical may designate —$CH_2$—$CH_2$—$NHCOCH_3$; or

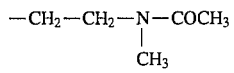

when groups $R_6$ and $R_7$ represent an acyl radical, the latter preferably being designated by the formyl, acetyl or propionyl radicals.

When group $R_3$ designates an alkyl radical, this latter is designated by methyl, ethyl, n-propyl, isopropyl, n-butyl or isobutyl.

The corresponding acid salts are preferably selected from hydrochlorides, sulfates or hydrobromides.

The following sulfated metaphenylenediamines having general formula (I) may be cited:

2-methyl-4-methylthio-1,3-diaminobenzene, denominated in accordance with IUPAC nomenclature as 2-methyl-4-methylsulfanyl-benzene-1,3-diamine, 2-ethyl-4-methylthio-1,3-diaminobenzene, denominated in accordance with IUPAC nomenclature as 2-ethyl-4-methylsulfanyl,benzene-1,3-diamine, 4-Chloro-6-propylthio-1,3-diaminobenzene, denominated in accordance with IUPAC nomenclature as 4-chloro-6-propylsulfanyl-benzene-1,3-diamine, 4,6-bis-methylthio-1,3-diaminobenzene, denominated in accordance with IUPAC nomenclature as 4,6-bis-methylsulfanyl-benzene-1,3-diamine, 4,6-bis-ethylthio-1,3-diaminobenzene, denominated in accordance with IUPAC nomenclature as 4,6-bis-ethylsulfanyl-benzene-1,3-diamine, 4,6-bis-trifluoromethylthio-1,3-[N,N'-bis(2,2,2-trifluoroethyl)]diaminobenzene, denominated in accordance with IUPAC nomenclature as N,N'-bis-(2,2,2-trifluoroethyl)-4,6-bis-trifluoromethylsulfanyl benzene-1,3-diamine, 4-methyl-6-methylthio-1,3-diaminobenzene, denominated in accordance with IUPAC nomenclature as 4-methyl-6-methylsulfanyl-benzene-1,3-diamine, 4-ethylthio-6-methyl-1,3-diaminobenzene, denominated in accordance with IUPAC nomenclature as 4-ethylsulfanyl-6-methyl-benzene-1,3-diamine, 4-carboxyethylthio-6-carboxymethylthio-1,3-diaminobenzene, denominated in accordance with IUPAC nomenclature as 3-(2,4-diamino- 5-carboxymethylsulfanyl-phenylsulfanyl)-propionic acid, 4,6-bis-carboxyethylthio-1,3-diaminobenzene, denominated in accordance with IUPAC nomenclature as 3-[2,4-diamino-5-( 2-carboxyethylsulfanyl)-phenylsulfanyl]-propionic acid, 2-methyl-4,6-bis-methylthio-1,3-diaminobenzene, denominated in accordance with IUPAC nomenclature as 2-methyl-4,6-bis-methylsulfanyl-benzene-1,3-diamine, 4,6-bis-ethylthio-2-methyl-1,3-diaminobenzene, denominated in accordance with IUPAC nomenclature as 4,6-bis-ethylsulfanyl-2-methyl-benzene-1,3-diamine, 4,6-bis-propylthio-2-methyl-1,3-diaminobenzene, denominated in accordance with IUPAC nomenclature as 4,6-bis propylsulfanyl-2-methyl-benzene-1,3-diamine, 4-methoxy-6-β-acetylaminoethylthio-1,3-diaminobenzene, denominated in accordance with IUPAC nomenclature as N-[2-(2,4-diamino-5-methoxy-phenylsulfanyl)-ethyl]-acetamide, 4-methoxy-6-methylthio-1,3-diaminobenzene, denominated in accordance with IUPAC nomenclature as 4-methoxy-6-methylsulfanyl-benzene-1,3-diamine, 5-chloro-2-methyl-4-β-acetylaminoethylthio-1,3-diaminobenzene, denominated in accordance with IUPAC nomenclature as N-[2-(2,4-diamino-6-chloro-3-methylphenylsulfanyl)ethyl]-acetamide, 4,6-bis-hydroxyethylthio-1,3-diaminobenzene, denominated in accordance with IUPAC nomenclature as 2-[2, 4-diamino-5-(2-hydroxyethylsulfanyl)-phenylsulfanyl]-ethanol.

Compounds with formula (I) may be used as coupling agents in the presence of known ortho and/or para type oxidation dye precursors which will dye the hair by oxidation dyeing in accordance with a process involving an oxidative condensation reaction between the precursors and the coupling agent.

Ortho and/or para type dye precursors are compounds which are not themselves dyes but form a dye through an oxidative condensation either with themselves or in the presence of a coupling agent or modifier.

These ortho or para type oxidation dye precursors are benzene derivatives or heterocyclic compounds comprising two functional amino groups or a hydroxy and an amino group in the ortho or para position relative to each other.

Ortho or para type oxidation dye precursors may be selected from paraphenylenediamines, paraaminophenols, para heterocyclic derivatives of pyridine, pyrimidine or pyrazole such as 2,5-diaminopyridine, 2-hydroxy 5-aminopyridine, 2,4,5,6-tetraaminopyrimidine, 4,5-diamino 1-methylpyrazole, 2-dimethylamino 4,5,6-triaminopyrimidine, orthoaminophenols and so-called double bases.

Regarding the paraphenylenediamines, compounds having formula (III) may in particular be cited:

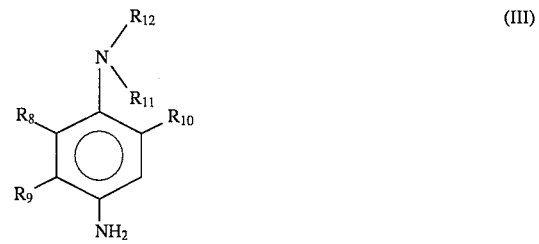

wherein:

$R_8, R_9, R_{10}$, which may be identical or different, represent a hydrogen or halogen atom, an alkyl radical, an alkoxy radical or a carboxy, sulfo or hydroxy ($C_1$–$C_4$) alkyl radical;

$R_{11}$ and $R_{12}$, which may be identical or different, represent a hydrogen atom, alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, morpholinoalkyl, or phenyl which may be para substituted by an amino group; or $R_{11}$ and $R_{12}$ together with the nitrogen atom to which they are bonded form a piperidino or morpholino heterocycle, providing that $R_8$ or $R_{10}$ represents a hydrogen atom when $R_{11}$ and $R_{12}$ do not represent hydrogen, including the salts of these compounds. The alkyl or alkoxy radicals preferably contain 1 to 4 carbon atoms and in particular designate methyl, ethyl, propyl, methoxy and ethoxy radicals.

Particular compounds with formula (III) are as follows:
paraphenylenediamine,
p-toluylenediamine,
methoxyparaphenylenediamine,
chloroparaphenylenediamine,
2,3-dimethylparaphenylenediamine,
2,6-dimethylparaphenylenediamine,
2,6-diethylparaphenylenediamine,
2,5-dimethylparaphenylene-diamine,
2-methyl 5-methoxyparaphenylenediamine,
2,6-dimethyl 5-methoxyparaphenylenediamine,
N,N-dimethylparaphenylenediamine,
N,N-diethylparaphenylenediamine,
N,N-dipropylparaphenylene-diamine,
3-methyl 4-amino N,N-diethylaniline,
N,N-di-(β-hydroxyethyl)paraphenylenediamine,
3-methyl 4-amino N,N-di-(β-hydroxyethyl)aniline,
3-chloro 4-amino N,N-di-(β-hydroxyethyl)aniline,
4-amino N,N-(ethyl, carbamylmethyl)aniline,
3-methyl 4-amino N,N-(ethyl, carbamylmethyl)aniline,
4-amino N,N-(ethyl, β-piperidinoethyl)aniline,
3-methyl 4-amino N,N-(ethyl, β-piperidinoethyl)aniline,
4-amino N,N-(ethyl, β-morpholinoethyl)aniline,
3-methyl 4-amino N,N-(ethyl, β-morpholinoethyl)aniline,
4-amino N,N-(ethyl, β-acetylaminoethyl)aniline,
4-amino N-(β-methoxyethyl)aniline,
3-methyl 4-amino N,N-(ethyl, β-acetylaminoethyl)aniline,
4-amino N,N-(ethyl, β-mesylaminoethyl)aniline, 3-methyl 4-amino N,N-(ethyl, β-mesylaminoethyl)aniline,
4-amino N,N-(ethyl, β-sulfoethyl)aniline,
3-methyl 4-amino N,N-(ethyl, β-sulfoethyl)aniline,
N-[(4'-amino)phenyl]-morpholine,
N-[(4'-amino)phenyl]piperidine,
2-hydroxyethylparaphenylenediamine,
fluoroparaphenylenediamine,
carboxyparaphenylenediamine,
sulfoparaphenylenediamine,
2-isopropylparaphenylenediamine,
2-n-propylparaphenylenediamine,
hydroxy-2-n-propylparaphenylenediamine,
2-hydroxymethylparaphenylenediamine,
N,N-dimethyl 3-methylparaphenylenediamine,
N,N-(ethyl,β-hydroxyethyl)paraphenylenediamine,
N-(dihydroxypropyl)-paraphenylenediamine,
N-4'-aminophenylparaphenylenediamine,
N-phenylparaphenylenediamine.

These paraphenylenediamines may be used either in the form of the free base or as a salt such as the hydrochloride, hydrobromide or sulfate.

Particular p-aminophenols which may be mentioned are as follows:
p-aminophenol,
2-methyl 4-aminophenol,
3-methyl 4-aminophenol,,
2-chloro 4-aminophenol,
3-chloro 4-aminophenol,
2,6-dimethyl 4-aminophenol,
3,5-dimethyl 4-aminophenol,
2,3-dimethyl 4-aminophenol,
2,5-dimethyl 4-aminophenol,
2-hydroxymethyl 4-aminophenol,
2-(β-hydroxyethyl) 4-aminophenol,
2-methoxy 4-aminophenol,
3-methoxy 4-aminophenol,
3-(β-hydroxyethoxy) 4-aminophenol,
2-methoxymethyl 4-aminophenol,
2-aminomethyl 4-aminophenol,
2-β-hydroxyethylaminomethyl 4-aminophenol,
2-ethoxymethyl 4-aminophenol,
2-(β-hydroxyethoxy)methyl 4-aminophenol.

The so-called double bases are bis-phenylalkylenediamines corresponding to the formula:

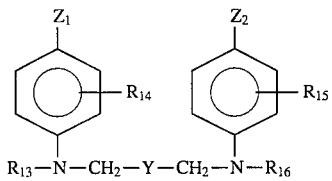

wherein:
$Z_1$ and $Z_2$, which may be identical or different, represent hydroxyl groups or $NHR_{17}$ groups where $R_{17}$ designates a hydrogen atom or a low alkyl radical;

$R_{14}$ and $R_{15}$, which may be identical or different, represent hydrogen atoms, halogen atoms or alkyl radicals;

$R_{13}$ and $R_{16}$, which may be identical or different, represent a hydrogen atom or an alkyl, hydroxyalkyl or aminoalkyl radical wherein the amino moiety may be substituted;

Y represents a radical selected from the following:

$-(CH_2)_n-$, $-(CH_2)_m-O-(CH_2)_m-$,

-continued
$-(CH_2)_q-CHOH-(CH_2)_q-$,

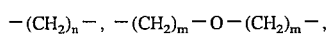

where n is a whole number between 0 and 8 and m, q and p are whole numbers between 0 and 4. This base may also be in the form of addition salts with acids.

The alkyl or alkoxy radicals indicated above preferably designate a group having one to four carbon atoms, in particular methyl, ethyl, propyl, methoxy and ethoxy, Particular compounds having formula (IV) which may be mentioned are as follows:
N,N'-bis-(β-hydroxyethyl) N,N'-bis-(4'-aminophenyl) 1,3-diamino 2-propanol,
N,N'-bis-(β-hydroxyethyl),
N,N'-bis-(4'-aminophenyl) ethylenediamine,
N,N'-bis-(4-aminophenyl) tetramethylenediamine,
N,N'-bis-(β-hydroxyethyl) N,N'-bis-(4-aminophenyl) tetramethylene-diamine,
N,N'-bis-(4-methylaminophenyl) tetramethylenediamine,
N,N'-bis-(ethyl) N,N'-bis-(4'-amino 3'-methylphenyl) ethylenediamine.

Particular orthoaminophenols which may be mentioned are as follows:
1-amino-2-hydroxybenzene,
6-methyl 1-hydroxy 2-aminobenzene,
4-methyl 1-amino 2-hydroxybenzene,
4-acetylamino 1-amino 2-hydroxybenzene.

Compounds with formula (I) are applied to the keratinous fibers, in particular human hair, as dye compositions which constitute the invention in a second aspect.

Compositions in accordance with the invention contain at least one sulfated metaphenylenediamine as defined above in an appropriate dye medium. Preferred compositions contain at least one sulfated metaphenylenediamine as defined above in association with at least one oxidation dye precursor as defined above.

Dye compositions in accordance with the invention may also contain, as well as the coupling agent having formula (I) as defined above, other known coupling agents such as metadiphenols, metaaminophenols, metaphenylenediamines different to those having formula (I) above, metaacylaminophenols, metaureidophenols, metacarbalkoxyaminophenols, α-napthol, indole derivatives, coupling agents containing an active methylene group such as β-ketones, and pyrazolones.

The following coupling agents may in particular be mentioned:
2,4-dihydroxyphenoxyethanol,
2,4-dihydroxyanisole,
metaaminophenol,
resorcinol monomethylether,
resorcinol,
2-methyl resorcinol,
2-methyl 5-aminophenol,
2-methyl 5-N-(β-hydroxyethyl) aminophenol,
2-methyl 5-N-(β-mesylaminoethyl) aminophenol,
2,6-dimethyl 3-aminophenol,
6-hydroxybenzomorpholine,
2,4-diaminoanisole,
2,4-diaminophenoxyethanol,
6-aminobenzomorpholine,
[2-N-(β-hydroxyethyl) amino 4-amino]-phenoxyethanol,
2-amino 4-N-(β-hydroxyethyl) aminoanisole,
(2,4-diamino)phenyl-β-γ-dihydroxypropylether, 2,4-diaminophenoxyethylamine,
1,3-dimethoxy 2,4-diaminobenzene,
1,3,5-trimethoxy 2,4-diaminobenzene,
1-amino 3,4-methylenedioxybenzene,
1-hydroxy 3,4-methylenedioxybenzene,
2-chloro 6-methyl 3-aminophenol,
2-methyl 3-aminophenol,
2-chlororesorcinol,
6-methoxy 3-hydroxyethylaminoaniline,
1-ethoxy 2-bis(β-hydroxyethyl)amino 4-aminobenzene,
3-diethylaminophenol,
1,3-dihydroxy 2-methylbenzene,
1-hydroxy 2,4-dichloro 3-aminobenzene,
4,6-di(hydroxyethoxy) 1,3-diaminobenzene,
4-methyl 6-ethoxy 1,3-diaminobenzene,
4-chloro 6-methyl 3-aminophenol,
6-chloro 3-trifluoroethylaminophenol, and salts thereof.

Direct dyes may be added to such compositions, as is known in the art, particularly to shade or enrich the lustre of the colors attained by the oxidation dye precursors. Examples of direct dyes are azo and anthraquinone dyes or nitro compounds of the benzene series.

The total amount of para and/or ortho type oxidation dye precursors plus the coupling agents used in dye compositions in accordance with the invention preferably comes to 0.3 to 7% by weight with respect to the weight of said composition. The composition of sulfated metaphenylenediamines of formula (I) may vary between and 3.5% by weight with respect to the total weight of the composition.

A preferred embodiment of a dye composition also contains a known anionic, cationic, non-ionic or amphoteric surfactant or mixture thereof.

These surfactants are present in proportions of between 0.5 and 55% by weight, preferably between 2 and 50% by weight with respect to the total composition weight.

These compositions may also contain organic solvents to solubilize components which are insufficiently soluble in water. Particular solvents which may be mentioned are $C_1$–$C_4$ low alkanols such as ethanol and isopropanol; glycerol; glycols or glycol ethers such as 2-butoxyethanol, ethyleneglycol, propyleneglycol, diethyleneglycol monoethylether and monomethylether, also aromatic alcohols such as benzyl alcohol or phenoxyethanol, as well as analogous products and their mixtures.

The solvents are preferably present in proportions of between 1 and 40% by weight, particularly between 5 and 30% by weight with respect to the total composition weight.

Thickening agents may be added to compositions in accordance with the invention, for example sodium alginate, gum arabic, acrylic acid polymers which may be reticulated, cellulose derivatives or heterobiopolysaccharides such as xanthane gum. Mineral thickening agents such as bentonite may also be used.

The thickening agents are preferably present in proportions of between 0.1 and 5%, in particular between 0.2 and 3% by weight with respect to the total composition weight.

Antioxidants which may be present in the compositions are preferably selected from sodium sulfite, thioglycolic acid, sodium bisulfite, dehydroascorbic acid, hydroquinone and homogentisic acid. These antioxidants are present in the composition in proportions of between 0.05 and 1.5% by weight with respect to the total composition weight.

The composition pH lies between 3 and 10.5. It is adjusted to the value desired using known alkalizing agents such as ammonia, alkaline carbonates, alkanolamines such as mono-, di- and triethanolamines as well as their derivatives, or sodium or potassium hydroxide, or standard acidifying agents, for example mineral or organic acids such as hydrochloric, tartaric, citric or phosphoric acid.

These compositions may further contain other cosmetically acceptable additives such as penetrating agents, sequestrum producing agents, perfume, buffers, etc.

Compositions in accordance with the invention take different forms, for example a liquid, cream, gel or any other form appropriate to dyeing keratinous fibers, in particular human hair. The compositions may be packaged in aerosol cans with a propellant to produce a foam.

Compounds of formula (I) are used in accordance with a method comprising applying a compound having formula (I) and oxidation dye precursors to the keratinous fibers in the presence of an oxidizing agent.

Dye compositions in accordance with the invention containing a para and/or ortho type oxidation dye precursor and a coupling agent of formula (I) are used in a method using an oxidizing agent as developer.

Using this method, when required for use the dye composition described above is mixed with an oxidizing solution in sufficient quantity to develop the color. The mixture thus obtained is then applied to the keratinous fibers, in particular human hair.

The pH of the composition applied to the hair preferably varies between 2 and 13. It is adjusted to the desired value using known alkalizing agents, for example ammonia, alkaline carbonates, alkanolamines such as mono-, di- and triethanolamine and their derivatives, or sodium or potassium hydroxide, or conventional acidifying agents such as mineral or organic acids, for example hydrochloric acid, tartaric acid, citric acid, phosphoric acid and sulfonic acid. The oxidizing solution contains, as the oxidizing agent, hydrogen peroxide, urea peroxide, peroxy salts such as ammonium persulfate, organic peracids and their salts or alkali metal bromides. A 20 volume solution of hydrogen peroxide is preferably used.

The mixture obtained is applied to the hair and left for 10 to 40, preferably 15 to 30 minutes. The hair is then rinsed, shampooed, rinsed again and dried.

The coupling agent of formula (I) defined above may also be used in a method involving several steps, one of these consisting in applying the or a mixture of the ortho and/or para oxidation dye precursor(s) and another consisting in applying a dye composition containing the coupling agent of formula (I).

The oxidizing agent may be introduced into the composition just before application in the second stage or it may be applied directly to the keratinous fibers in a third stage. Application, pH, washing and drying conditions are as indicated above.

A further aspect of the invention is constituted by novel sulfated metaphenylenediamines having the formula:

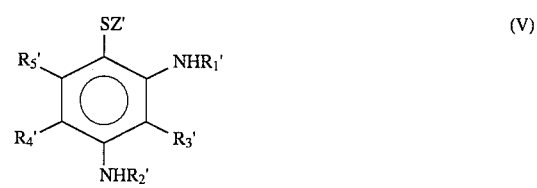

(V)

wherein:

Z' represents a $C_1$–$C_{18}$ alkyl radical, an aralkyl radical wherein the alkyl radical is $C_1$–$C_6$, a $C_1$–$C_6$ monohydroxyalkyl or $C_2$–$C_6$ polyhydroxyalkyl radical, an aryl radical, a $C_1$–$C_4$ fluoroalkyl radical, an aminoalkyl radical having the formula:

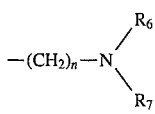

(II)

wherein n is a whole number from 1 to 6 inclusive;

$R'_6$ and $R'_7$, which may be identical or different, represent a hydrogen atom or a $C_1$–$C_4$ alkyl radical, a $C_1$–$C_4$ hydroxyalkyl radical or a $C_1$–$C_6$ acyl radical;

$R'_1$ and $R'_2$, which may be identical or different, represent a hydrogen atom, a $C_1$–$C_6$ alkyl radical, a $C_1$–$C_6$ monohydroxyalkyl radical, a $C_2$–$C_6$ polyhydroxyalkyl radical, a $C_1$–$C_6$ monocarbamylalkyl radical, a $C_1$–$C_6$ dialkylcarbamyl radical, a $C_1$–$C_6$ aminoalkyl radical, an acylaminoalkyl ($C_1$–$C_4$) radical, a carbalkoxy($C_2$–$C_6$)alkyl($C_1$–$C_4$) radical, a $C_1$–$C_6$ carbamyl or monoalkyl radical, or a $C_1$–$C_4$fluoroalkyl radical;

$R'_3$ represents a hydrogen atom or a $C_1$–$C_4$ alkyl radical;

$R'_4$ and $R'_5$, which may be identical or different represent a hydrogen atom, a halogen, a $C_1$–$C_4$alkoxy radical, a $C_1$–$C_4$hydroxyalkyl radical, a —SR radical where R represents a $C_1$–$C_4$hydroxyalkyl radical, a $C_2$–$C_6$ polyhydroxyalkyl radical, an aralkyl radical wherein the alkyl radical is $C_1$–$C_6$, an aryl radical, an aminoalkyl radical having formula:

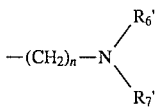

(II)

wherein n is a whole number from 1 to 6 inclusive;

$R'_6$ and $R'_7$, which may be identical or different, represent a hydrogen atom or a $C_1$–$C_4$ alkyl radical, a $C_1$–$C_4$ hydroxyalkyl radical or a $C_1$–$C_6$ acyl radical, providing that $R'_4$ and $R'_5$ do not simultaneously designate a hydrogen atom;

and when either $R'_4$ or $R'_5$ designates a chlorine atom, $R'_3$ represents an alkyl radical.

Particular compounds of formula (V) which may be mentioned are as follows:

4-methoxy-6-β-acetylaminoethylthio-1,3-diaminobenzene, denominated in accordance with IUPAC nomenclature as N-[2-(2,4-diamino- 5-methoxyphenylsulfanyl-ethyl]-acetamide, 4-methoxy-6-methylthio-1,3-diaminobenzene, denominated in accordance with IUPAC nomenclature as 4-methoxy-6-methylsulfinyl-benzene-1,3-diamine, 5-chloro-2-methyl-4-β-acetylaminoethylthio-1,3-diaminobenzene, denominated in accordance with IUPAC nomenclature as N-[2-(2,4-diamino-6-chloro-3-methylphenylsulfanyl)ethyl]-acetamide, 4,6-bis-hydroxyethylthio-1,3-diaminobenzene, denominated in accordance with IUPAC nomenclature as 2-[2, 4-diamino-5-( 2-hydroxyethylsulfanyl)-phenylsulfanyl]-ethanol.

Sulfated metaphenylenediamines with formula (V) or their salts may be prepared by a multistage process.

According to a first process, in a first step 1,3-dichloro-4,6-dinitrobenzene is reacted in the presence of a base such as potash or potassium carbonate with a thiol having formula (VI):

$Z_1$—SH (VI)

wherein $Z_1$ represents a $C_1$–$C_{18}$ alkyl radical, an aralkyl radical wherein the alkyl radical is $C_1$–$C_6$, a $C_1$–$C_6$ monohydroxyalkyl radical, a $C_2$–$C_6$ polyhydroxyalkyl radical, an aryl radical or a group having formula (VII):

(VII)

wherein $R'_6$ and n have the designations indicated above for formula (V), and $R_{17}$ represents a hydrogen atom or a $C_1$–$C_3$ alkyl radical; in a second step, the nitro substituents on a compound of formula (VIII):

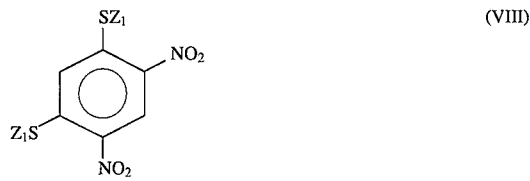

(VIII)

are reduced to prepare a compound having formula (IX):

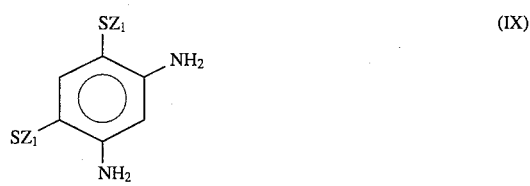

(IX)

wherein $Z_1$ has the meaning indicated above; if necessary, in a third step depending on the sulfated metaphenylenediamine with formula (I) to be obtained, the following is carried out:

a) either monosubstitution of the aromatic amines to produce compound (V) where $R'_1$ and/or $R'_2$ are other than H; or b) acid hydrolysis of compound (IX) where Z' represents a group with formula (VII) to obtain compound (X):

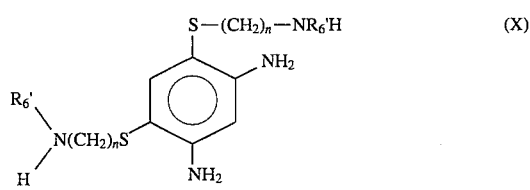

(X)

wherein $R'_6$ and h have the meanings given above, although $R'_6$ may not designate the $C_1$–$C_6$ acyl radical; the nuclear amines may then be monosubstituted, or c) first substituting the extranuclear amine in compound (IX) to produce compound (XI):

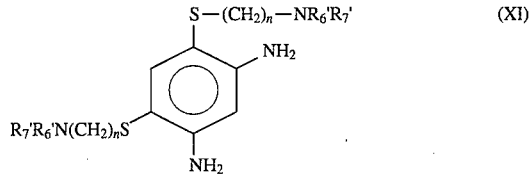

(XI)

wherein $R'_6$, $R'_7$ and n have the meanings given above; the nuclear amines may then be monosubstituted.

In a second process, a first substituted compound (XII):

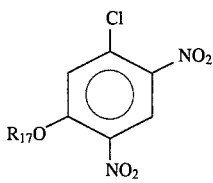 (XII)

wherein $R_{17}$ represents a $C_1$–$C_4$ alkyl group, is reacted with a thiol of formula:

$Z_1$—SM (XIII)

wherein M is an alkali metal and $Z_1$ has the meaning indicated above.

In a second step, the nitro substituent in a compound of formula (XIV):

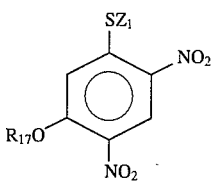 (XIV)

is reduced to prepare the compound of formula (XV):

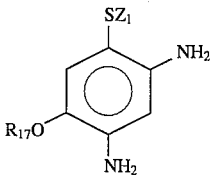 (XV)

wherein $R_{17}$ and $Z_1$ have the meanings given above; if necessary, in a third step depending on the sulfated metaphenylenediamine of formula (V) to be prepared, monosubstitution of the aromatic amine is carried out to obtain a compound of formula (V) where $R'_1$ or $R'_2$ is other than H.

In the first step of a third process, a polysubstituted 2,4-dinitrobenzene having formula (XVI):

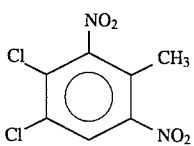 (XVI)

is reacted with a thiol of formula:

$Z_1$—SM (XIII)

wherein M is an alkali metal and $Z_1$ has the meaning given above.

In a second step, the nitro substituents on a compound of formula (XVII):

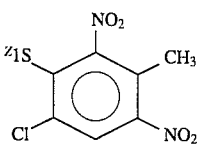 (XVII)

are reduced to prepare a compound having formula (XVIII):

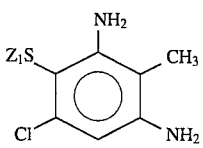 (XVIII)

wherein $Z_1$ has the meaning given above.

Reduction of the nitro groups is preferably carried out using iron in an acetic medium or cyclohexene in the presence of a palladium-carbon catalyst or powdered zinc in the presence of ethanol and ammonium chloride or by any other conventional reduction process.

Substitution of the aromatic amines or the extranuclear amine may be carried out by reaction with ethyl bromide, glycol bromohydrin, ethyl chloroformate, β-chloroacetamide, or acetic anhydride, for example.

DETAILED DESCRIPTION OF THE INVENTION

The following examples illustrate but do not limit the scope of the invention.

Preparation Example 1

Preparation of the monohydrate of 4-methoxy 6-methylthio 1,3-diaminobenzene dihydrochloride, denominated in accordance with the IUPAC nomenclature as 4-methoxy 6-methylsulfanyl-benzene 1,3-diamine. dihydrochloride, monohydrate.

Step 1: Synthesis of (5-methoxy 2,4-dinitrophenyl)-methylsulfane.

A solution of 23.2 g (0.1 mole) 1-chloro 5-methoxy-2,4-dinitrobenzene in 60 ml dimethoxyethane was added dropwise over one hour to a suspension of sodium thiomethylate (0.15 mole) in 120 ml dimethoxyethane at room temperature.

The reaction was exothermic; the temperature was maintained between 23 and 25° C.

After addition was complete, the suspension was agitated for half an hour then poured into 60 ml of iced water. The crystallized precipitate was dried, taken up in water, washed with isopropanol and recrystallized from boiling dimethoxyethane.

16.9 g of yellow crystals were obtained which melted at 161° C. and had the following elemental analysis for $C_8H_8N_2O_5S$:

|  | C% | H% | N% | O% | S% |
| --- | --- | --- | --- | --- | --- |
| Calculated | 39.34 | 3.30 | 11.47 | 32.76 | 13.13 |
| Found | 39.54 | 3.28 | 11.44 | 32.71 | 13.20 |

Step 2: reduction.

A mixture of 2.2 g ammonium chloride, 16.5 ml water, 140 ml 96° alcohol and 41 g finely powdered zinc was heated under reflux. Portions of (5-methoxy 2,4-dinitrophenyl)methylsulfane obtained from step 1 (11.0 g, 0.045 mole) were added so as to maintain the reflux without heating. The reaction was exothermic.

Following addition, the mixture was refluxed for a further half an hour. The reaction mixture was filtered whilst boiling into 17 ml of about 6N hydrochloric acid in absolute alcohol.

The dichlorohydrate of 4-methoxy 6-methylsulfanyl-benzene-1,3-diamine, monohydrate crystallized on cooling the filtrate.

After vacuum drying over potash, 7.0 g of white crystals were obtained which melted at 198°–203° C. with decomposition. Elemental analysis calculated for $C_8H_{16}Cl_2N_2O_2S$ was as follows:

|  | C% | H% | N% | O% | S% | Cl% |
|---|---|---|---|---|---|---|
| Calculated | 34.92 | 5.86 | 10.18 | 11.63 | 11.65 | 25.77 |
| Found | 35.23 | 5.87 | 10.23 | 11.30 | 11.81 | 25.63 |

Preparation Example 2

Preparation of the monohydrate of 4-methoxy 6-β-acetoaminoethylthio 1,3-diaminobenzene dihydrochloride, denominated in accordance with the IUPAC nomenclature as N-[2-(2,4-diamino-5-methoxy-phenylsulfanyl)-ethyl]-acetamide dihydrochloride, monohydrate.

Step 1: Synthesis of N-[2-(5-methoxy 2,4-dinitro-phenylsulfanyl) ethyl]-acetamide.

10 g of powdered potash were dissolved in a solution of 19.0 g (0.15 mole) N-(2-mercaptoethyl)-acetamide in 100 ml dimethoxyethane at 40° C.

After cooling to 15° C., a solution of 23.2 g (0.1 mole) 1-chloro-5-methoxy-2,4-dinitrobenzene in 60 ml dimethoxyethane was added dropwise over thirty minutes whilst holding the temperature between 15°and 20° C.

The suspension was agitated for one hour then poured into 500 ml of iced water.

The crystallized precipitate was dried, taken up in water then in isopropyl alcohol and recrystallized from 96° boiling alcohol.

23.2 g of yellow crystals were obtained which melted at 185° C. Elemental analysis calculated for $C_{11}H_{13}N_3O_6S$ gave the following:

|  | C% | H% | N% | O% | S% |
|---|---|---|---|---|---|
| Calculated | 41.90 | 4.16 | 13.33 | 30.45 | 10.17 |
| Found | 41.94 | 4.15 | 13.38 | 30.54 | 10.09 |

Step 2: Reduction

Reduction was carried out using the method described in example 1 step 2.

White crystals of the dichlorohydrate of N-[2-(2,4-diamino 5-methoxy-phenylsulfanyl)-ethyl]-acetamide monohydrate were obtained, which melted with decomposition at 183°–187° C. Elemental analysis calculated for $C_{11}H_{21}N_3O_3SCl$ was as follows:

|  | C% | H% | N% | O% | S% | Cl% |
|---|---|---|---|---|---|---|
| Calculated | 38.16 | 6.11 | 12.13 | 13.86 | 9.26 | 20.48 |
| Found | 37.83 | 6.48 | 11.93 | 14.12 | 9.25 | 20.37 |

Preparation Example 3

Preparation of 4,6-bis-hydroxyethylthio-1,3-diaminobenzene, denominated in accordance with the IUPAC nomenclature as 2-[2,4-diamino 5-(2-hydroxyethylsulfanyl)-phenylsulfanyl]-ethanol.

Step 1: Synthesis of 2-[5-(2-hydroxyethylsulfanyl) 2,4-dinitrophenylsulfanyl]ethanol.

A mixture of 34.5 g potassium carbonate, 8 g 2-mercaptoethanol and 100 ml dioxane was heated together to 60° C.

11.9 g (0.05 mole) of 1,5-dichloro-2,4-dinitrobenzene were added and heating maintained at 60° C. for one hour then one hour at 100° C.

The reaction mixture was then poured into 500 ml of iced water.

The crystallized precipitate was dried, taken up in water and vacuum dried over phosphorus pentoxide.

9.0 g of orange-yellow crystals which melted at 149° C. were obtained after recrystallization.

Step 2: Reduction

Reduction was carried out using the method described in example 1, step 2.

White crystals (81%) of 2-[2,4-diamino-5-(2-hydroxyethylsulfanyl)-phenylsulfanyl]-ethanol were obtained which melted at 144° C. Elemental analysis calculated for $C_{10}H_{16}N_2O_2S_2$ was as follows:

|  | C% | H% | N% | O% | S% |
|---|---|---|---|---|---|
| Calculated | 46.13 | 6.19 | 10.76 | 12.29 | 24.63 |
| Found | 46.21 | 6.07 | 10.67 | 12.42 | 24.57 |

Preparation Example 4

Preparation of 5-chloro 2-methyl 4-β-acetaminoethylthio 1,3-diaminobenzene, denominated in accordance with the IUPAC nomenclature as N-[2-(2,4-diamino 6-chloro 3-methylphenylsulfanyl)-ethyl]-acetamide.

Step 1: Synthesis of N-[2-(6-chloro-3-methyl 2,4-dinitrophenyl-sulfanyl)-ethyl]-acetamide.

This synthesis was carried out using the method described for example 2, step 1. Starting from 30.1 g (0.12 mole) of 1,2-dichloro-4-methyl 3,5-dinitrobenzene, 15.5 g of pale yellow crystals were obtained which melted at 152° C. (recrystallized from ethyl acetate). Elemental analysis calculated for $C_{11}H_{12}ClN_3OS$ was as follows:

|  | C% | H% | N% | O% | S% | Cl% |
|---|---|---|---|---|---|---|
| Calculated | 39.59 | 3.62 | 12.59 | 23.97 | 9.61 | 10.62 |
| Found | 39.67 | 3.62 | 12.63 | 23.84 | 9.69 | 10.56 |

Step 2: Reduction

Reduction was carried out using the method described for example 1, step 2.

White crystals of N-[2-(2,4-diamino 6-chloro 3-methylphenylsulfanyl)-ethyl]-acetamide were obtained (recrystallization from 96° ethanol) which melted at 111° C. Elemental analysis calculated for $C_{11}H_{16}ClN_3OS$ was as follows:

|  | C% | H% | N% | O% | S% | Cl% |
|---|---|---|---|---|---|---|
| Calculated | 46.26 | 5.89 | 15.35 | 5.84 | 11.71 | 12.95 |
| Found | 48.31 | 5.92 | 15.27 | 5.92 | 11.69 | 12.87 |

COMPOSITION EXAMPLES

Example 1

| | |
|---|---|
| Monohydrate of 4-methoxy 6-β-acetylaminoethyl thio-1,3-diaminobenzene dihydrochloride | 1.038 g |
| 2,6-dimethyl paraphenylenediamine dihydrochloride | 0.627 g |
| Oleic alcohol polyglycerolated to 2 moles glycerol | 4 g |
| Oleic alcohol polyglycerolated to 4 moles glycerol | 5.7 g |
| Oleic acid | 3 g |
| Oleic amine oxyethylenated to 2 moles ethylene oxide sold under the trade name ETHOMEEN O12 ® by Akzo | 7 g |
| Sodium salt of diethylaminopropyl lauryl-amino succinamate | 3 g AM |
| Oleic alcohol | 5 g |
| Oleic acid diethanolamide | 12 g |
| Propylene glycol | 3.5 g |
| Ethyl alcohol | 7 g |
| Dipropylene glycol | 0.5 g |
| Propylene glycol monomethyl ether | 9 g |
| Sodium metabisulfite, 35% aqueous solution | 0.45 g AM |
| Ammonium acetate | 0.8 g |
| Antioxidant, sequestrum producer | q.s |
| Perfume, preservative | q.s |
| Monoethanolamine | q.s pH: 9.8 |
| Demineralized water q.s.p. | 100 g |

The above composition was mixed just before use with an equal weight of 20 vol hydrogen peroxide whose pH had been adjusted to between 1 and 1.5 by addition of orthophosphoric acid. The pH of the mixture was equal to 6.5. This was applied to gray hair with 90% white and left for 30 minutes at room temperature. The hair was rinsed, shampooed, rinsed again then dried. It had been dyed blue.

Example 2

This was similar to example 1, replacing the 1.038 g of the monohydrate of 4-methoxy-6-β-acetylaminoethylthio 1,3-diaminobenzene dihydrochloride with 0.821 g of 5-chloro 2-methyl 4-β-acetylaminoethylthio 1,3-diaminobenzene.

Under identical dyeing conditions to those described for example 1, gray hair with 90% white was dyed unpolished gold.

Example 3

The following dye composition was prepared:

| | |
|---|---|
| monohydrate of 4-methoxy 6-methylthio 1,3-diaminobenzene dihydrochloride | 0.55 g |
| Paraphenylenediamine | 0.216 g |
| Octyldodecanol sold under the trade name EUTANOL D ® by HENKEL | 8 g |
| Oleic alcohol | 20 g |
| Monoethanolamiine laurylethersulfate, sold under the trade name SIPON LM 35 ® by Henkel | 3 g |
| Ethyl alcohol | 10 g |
| Benzyl alcohol | 10 g |
| Cetylstearyl alcohol oxyethylenated to 33 moles | 2.4 g |
| ethylene oxide sold under the trade name SIMULSOL GS by Seppic | |
| Ethylenediamine tetracetic acid | 0.2 g |
| Cationic polymer solution containing the following: | 3.7 g |

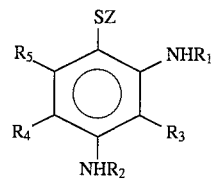
to 60% M.A.

| | |
|---|---|
| monoethanolamine | 7.5 g |
| Diethanolamide of linoleic acid sold under the trade name COMPERLAN F ® by Henkel | 8 g |
| Ammonia solution, 20% NH₃ | 10.2 g |
| Sodium metabisulfite, 35% aqueous solution | 1.3 g |
| Hydroquinone | 0.15 g |
| 1-phenyl 3-methyl 5-pyrazolone | 0.2 g |
| Demineralized water q.s.p. | 100 g |

This composition was mixed just before use with an equal weight of 20 vol hydrogen peroxide with a pH of 3. The pH of the mixture was equal to 9.5. This was applied to permed gray hair and left for 30 minutes at room temperature. The hair was then rinsed, shampooed and dried. It was dyed a dull bluish gray.

We claim:

1. A composition for dyeing human hair comprising, in a vehicle suitable for dyeing said human hair, (a) at least one coupler comprising a sulfated metaphenylenediamine having the formula

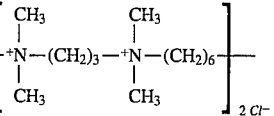 (I)

wherein

Z represents $C_1$–$C_{18}$ alkyl, aralkyl wherein the alkyl moiety has 1–6 carbon atoms, $C_1$–$C_6$ monohydroxyalkyl, $C_2$–$C_6$ polyhydroxyalkyl, aryl, $C_1$–$C_4$ fluoroalkyl, aminoalkyl having the formula

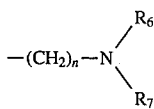

wherein n is a whole number ranging from 1 to 6 and $R_6$ and $R_7$, each independently, represent hydrogen, $C_1$–$C_4$ alkyl, $C_1$–$C_4$ hydroxyalkyl or $C_1$–$C_6$ acyl;

$R_1$ and $R_2$, each independently, represent hydrogen, $C_1$–$C_6$ alkyl, $C_1$–$C_6$ monohydroxyalkyl, $C_2$–$C_6$ polyhydroxyalkyl, $C_1$–$C_6$ monocarbamylalkyl, $C_1$–$C_6$ dialkylcarbamyl, $C_1$–$C_6$ aminoalkyl, acylamino ($C_1$–$C_4$) alkyl, carb($C_2$–$C_6$)alkoxy($C_1$–$C_4$)alkyl, carbamyl, mono($C_{1-6}$)alkyl carbamyl or $C_1$–$C_4$ fluoroalkyl;

$R_3$ represents hydrogen or $C_1$–$C_4$ alkyl;

$R_4$ represents hydrogen, $C_1$–$C_4$ alkyl, $C_1$–$C_4$ alkoxy, $C_1$–$C_4$ hydroxyalkyl, halogen or —SZ' wherein Z' represents dodecyl; hexadecyl; aralkyl wherein the alkyl moiety has 1–6 carbon atoms; $C_1$–$C_6$ monohydroxyalkyl; $C_2$–$C_6$ polyhydroxyalkyl; aryl; $C_1$–$C_4$ fluoroalkyl; amino alkyl having the formula

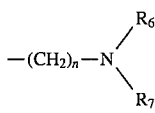

wherein n is a whole number ranging from 1 to 6 and $R_6$ and $R_7$ each independently represent hydrogen, $C_1$–$C_4$ alkyl, $C_1$–$C_4$ hydroxyalkyl or $C_1$–$C_6$ acyl; and $R_5$ represents hydrogen, $C_1$–$C_4$ alkyl, $C_1$–$C_4$ alkoxy, $C_1$–$C_4$ hydroxyalkyl, halogen or —SZ wherein Z has the meaning given above;

with the proviso that at least one of $R_3$, $R_4$ and $R_5$ is other than hydrogen;

or an acid addition salt of said sulfated metaphenylenediamine of formula (I), or both said sulfated metaphenylenediamine of formula (I) and said acid addition salt thereof;

said sulfated metaphenylenediamine or said acid addition salt thereof, or both, being present in an amount ranging from 0.05 to 3.5 percent by weight based on the total weight of said composition; and (b) at least one of an ortho or para oxidation dye precursor present in an amount effective to dye said human hair by oxidative condensation reaction between said precursor and said coupler.

2. The composition of claim 1, which also includes a further coupler selected from the group consisting of a metadiphenol, a metaaminophenol, a metaphenylenediamine other than the sulfated metaphenylenediamine of formula (I), a metaacylaminophenol, a metaureidophenol, a metacarbalkoxyaminophenol, α-naphthol, an indole derivative and a coupling agent having an active methylene group, and wherein said ortho or para type oxidation dye precursor, or both, and said coupler of formula I and said further coupler are present in a total amount ranging from 0.3 to 7 percent by weight based on the total weight of said composition.

3. The composition of claim 1 wherein Z represents methyl; ethyl; propyl; butyl; dodecyl; hexadecyl; benzyl; phenyl; the group consisting of

—CH$_2$—CH$_2$—OH; —CH$_2$—CHOH—CH$_2$—OH; —CH$_2$—CHOH—CH$_3$;

—CH$_2$—CH$_2$—NH$_2$; —CH$_2$—CH$_2$—NHCH$_3$; —CH$_2$—CH$_2$—NH—COCH$_3$; and

—CH$_2$—CH$_2$—N—COCH$_3$;
         |
         CH$_3$ and when $R_6$ or $R_7$ represents acyl said acyl represents a formyl, acetyl or propionyl group.

4. The composition of claim 1 wherein said sulfated metaphenylenediamine of formula (I) is selected from the group consisting of
2-methyl-4-methylthio-1,3-diaminobenzene,
2-ethyl-4-methylthio-1,3-diaminobenzene,
4-chloro-6-propylthio-1,3-diaminobenzene,
4,6-bis-trifluoromethylthio-1,3-[N,N'-bis-(2',2',2'-trifluoroethyl)]-diaminobenzene,
4-methyl-6-methylthio-1,3-diaminobenzene,
4-ethylthio-6-methyl-1,3-diaminobenzene,
4-carboxyethylthio-6-carboxymethylthio-1,3-diaminobenzene,
4,6-bis-carboxyethylthio-1,3-diaminobenzene,
4-methoxy-6-β-acetylaminoethylthio-1,3-diaminobenzene,
4-methoxy-6-methylthio-1,3-diaminobenzene,
5-chloro-2-methyl-4-β-acetylaminoethylthio-1,3-diaminobenzene,
4,6-bis-hydroxyethylthio-1,3-diaminobenzene,
and an acid salt thereof.

5. The composition of claim 1 wherein said acid salt is selected from the group consisting of a hydrochloride, a sulfate and a hydrobromide.

6. The composition of claim 1 wherein said oxidation dye precursor is selected from the group consisting of a paraphenylenediamine, a paraaminophenol, a para heterocyclic precursor derived from pyridine, pyrimidine or pyrazole, an orthoaminophenol and a bis-phenylalkylenediamine.

7. The composition according to claim 1 which also contains an additive selected from a cationic, anionic, nonionic or amphoteric surfactant or mixture thereof in an amount ranging from 0.5 to 55 percent by weight based on the total weight of said compositions an organic solvent in an amount ranging from 1 to 40 percent by weight based on the total weight of said composition; a direct dye; a thickening agent in an amount ranging from 0.1 to 5 percent by weight based on the total weight of said composition; and an antioxidant in an amount ranging from 0.05 to 1.5 percent by weight based on the total weight of said composition.

8. The composition of claim 1 in the form of a liquid, cream, gel or packaged in an aerosol container in the presence of a propellant and capable of forming a foam.

9. A method for dyeing human hair comprising applying to said hair a dye composition comprising, in a vehicle suitable for dyeing said human hair, (a) at least one coupler comprising a sulfated metaphenylenediamine having the formula

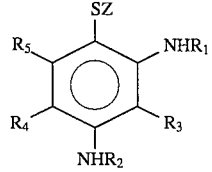

wherein

Z represents $C_1$–$C_{18}$ alkyl, aralkyl wherein the alkyl moiety has 1–6 carbon atoms, $C_1$–$C_6$ monohydroxyalkyl, $C_2$–$C_6$ polyhydroxyalkyl, aryl, $C_1$–$C_4$ fluoroalkyl, aminoalkyl having the formula

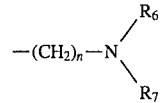

wherein n is a whole number ranging from 1 to 6 and $R_6$ and $R_7$, each independently, represent hydrogen, $C_1$–$C_4$ alkyl, $C_1$–$C_4$ hydroxyalkyl or $C_1$–$C_6$ acyl;

$R_1$ and $R_2$, each independently, represent hydrogen, $C_1$–$C_6$ alkyl, $C_1$–$C_6$ monohydroxyalkyl, $C_2$–$C_6$ polyhydroxyalkyl, $C_1$–$C_6$ monocarbamylalkyl, $C_1$–$C_6$ dialkylcarbamyl, $C_1$–$C_6$ aminoalkyl, acylamino ($C_1$–$C_4$) alkyl, carb($C_2$–$C_6$)alkoxy($C_1$–$C_4$)alkyl, carbamyl, mono($C_1$–$C_6$)alkyl carbamyl or $C_1$–$C_4$ fluoroalkyl;

$R_3$ represents hydrogen or $C_1$–$C_4$ alkyl;

$R_4$ represents hydrogen, $C_1$–$C_4$ alkyl, $C_1$–$C_4$ alkoxy, $C_1$–$C_4$ hydroxyalkyl, halogen or —SZ' wherein Z' represents dodecyl; hexadecyl; aralkyl wherein the alkyl moiety has 1–6 carbon atoms; $C_1$–$C_6$ monohydroxyalkyl; $C_2$–$C_6$ polyhydroxyalkyl; aryl; $C_1$–$C_4$ fluoroalkyl; amino alkyl having the formula

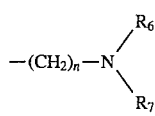

wherein n is a whole number ranging from 1 to 6 and $R_6$ and $R_7$ each independently represent hydrogen, $C_1$–$C_4$ alkyl, $C_1$–$C_4$ hydroxyalkyl or $C_1$–$C_6$ acyl; and $R_5$ represents hydrogen, $C_1$–$C_4$ alkyl, $C_1$–$C_4$ alkoxy, $C_1$–$C_4$ hydroxyalkyl, halogen or —SZ wherein Z has the meaning given above;

with the proviso that at least one of $R_3$, $R_4$ and $R_5$ is other than hydrogen;

or an acid addition salt of said sulfated metaphenylenediamine of formula (I), or both said sulfated metaphenylenediamine of formula (I) and said acid addition salt thereof;

said sulfated metaphenylenediamine or said acid addition salt thereof, or both, being present in an amount ranging from 0.05 to 3.5 percent by weight based on the total weight of said composition; and (b) at least one of an ortho or para oxidation dye precursor present in an amount effective to dye said human hair by oxidative condensation reaction between said precursor and said coupler, said dye composition also containing an oxidizing agent selected from the group consisting of hydrogen peroxide, urea peroxide, a peroxy salt, an organic per acid or a salt thereof and an alkali metal bromide.

10. The method according to claim 9 wherein said ortho or para type oxidation dye precursor, or both, and said sulfated metaphenylenediamine in said medium are mixed just before use with an amount of an oxidizing solution sufficient to develop said dye, the resultant composition having a pH ranging from 2 to 13.

11. The method of claim 10 wherein said composition is left on the hair for a period of time ranging from 10 to 40 minutes, and thereafter the hair is rinsed, shampooed, rinsed again and dried.

* * * * *